US011339423B2

(12) United States Patent
Bishop et al.

(10) Patent No.: US 11,339,423 B2
(45) Date of Patent: May 24, 2022

(54) SYSTEMS AND METHODS FOR DATA STORAGE IN NUCLEIC ACIDS

(71) Applicants: Bryan Bishop, Austin, TX (US); Tudor Boloni, Santa Monica, CA (US); Kent Kemmish, Menlo Park, CA (US); Maxwell Berry, Encinitas, CA (US)

(72) Inventors: Bryan Bishop, Austin, TX (US); Tudor Boloni, Santa Monica, CA (US); Kent Kemmish, Menlo Park, CA (US); Maxwell Berry, Encinitas, CA (US)

(73) Assignee: Bryan Bishop, Austin, TX (US)

( * ) Notice: Subject to any disclaimer, the term of this patent is extended or adjusted under 35 U.S.C. 154(b) by 468 days.

(21) Appl. No.: 16/272,734

(22) Filed: Feb. 11, 2019

(65) Prior Publication Data

US 2019/0284620 A1     Sep. 19, 2019

Related U.S. Application Data

(60) Provisional application No. 62/644,533, filed on Mar. 18, 2018.

(51) Int. Cl.
*C12Q 1/6844* (2018.01)
*C12Q 1/682* (2018.01)
*G06N 3/12* (2006.01)

(52) U.S. Cl.
CPC .......... *C12Q 1/6844* (2013.01); *C12Q 1/682* (2013.01); *G06N 3/123* (2013.01); *C12Q 2531/125* (2013.01); *C12Q 2533/10* (2013.01)

(58) Field of Classification Search
CPC .................. C12Q 1/6844; C12Q 1/682; C12Q 2531/125; C12Q 2533/10; C12Q 2563/185; G06N 3/123
See application file for complete search history.

(56) References Cited

U.S. PATENT DOCUMENTS 10,839,295 B2 * 11/2020 Shen ..................... G06F 40/123
10,982,276 B2 *  4/2021 Efcavitch ............. G11C 7/1006

OTHER PUBLICATIONS

Clark, Peter Graham, "A hypothetical protocol for DIYBIO DNA synthesis", May 29, 2016.
Lubock, Nathan B. et al., "A systematic comparison of error correction enzymes by next-generation sequencing", Nucleic Acids Research, 2017.
Chari, Raj et al., "Beyond editing to writing large genomes", Nature Review—Genetics, 2017.
Perli, Samuel D. et al., "Continuous genetic recording with self-targeting CRISPR-Cas in human cells", Science, Aug. 18, 2016.
Palluk, Sebastian et al., "De novo DNA synthesis using polymerase-nucleotide conjugates", Nature Biotechnology, Jun. 18, 2018.
Lee, Henry H. et al., "Enzymatic DNA synthesis for digital information storage", 2018.
Hessel, Andrew et al., "Exploring Template-Independent Polymerases for Automated DNA Synthesis", 2010.
Bishop, Bryan et al., "Summary Report—Technology Working Group Meeting on future DNA synthesis technology", Oct. 22, 2017.
Farzadfard, Fahim et al., "Genomically Encoded Analog Memory with Precise In vivo DNA Writing in Living Cell Populations", Science, Nov. 14, 2014.
De Paz, Alexandra M. et al., "High-resolution mapping of DNA polymerase fidelity using nucleotide imbalances and next-generation sequencing", Nucleic Acids Research, 2018.
Kosuri, Sriram et al., "Large-scale de novo DNA synthesis: technologies and applications", Nature Methods, vol. 11, No. 5, May 2014.
Zamft, Bradley Michael et. al., "Measuring Cation Dependent DNA Polymerase Fidelity Landscapes by Deep Sequencing", PLOS One, vol. 7, Issue 8, Aug. 2012.
Shipman, Seth L. et al., "Molecular recordings by directed CRISPR Spacer acquisition", Science Mag, Jun. 9, 2016.
Sheth, Ravi U. et al., "Multiplex recording of cellular events overtime on CRISPR biological tape", Science Mag, Nov. 23, 2017.
Zhirnov, Victor et al. "Nucleic acid memory", Nature Materials, vol. 15, Apr. 2016.
Cybulski, Thaddeus R. et al., "Nucleotide-time alignment for molecular recorders", PLOS Computational Biology, May 1, 2017.
Kording, Konrad P., "Of Toasters and Molecular Ticker Tapes", PLoS Computational Biology, vol. 7, Issue 12, Dec. 2011.
Glaser, Joshua I. et al., "Statistical Analysis of Molecular Signal Recording", PLOS Computational Biology, vol. 9, Issue 7, Jul. 2013.
Frieda, Kirsten L. et al., "Synthetic recording and in situ readout of lineage information in single cells", Nature, 2016.
Mohsen, Michael G. et al., "The Discovery of Rolling Circle Amplification and Rolling Circle Transcription", Acc Chem Res, Nov. 15, 2016.
Mayer, Clemens et al., "An Epigenetics-Inspired DNA-Based Data Storage System", Angew. Chern. Int. Ed., 2016.
Marblestone, Adam, "molecular ticker-tapes", Apr. 29, 2013.
Jensen, Michael A. et al., "Template-Independent Enzymatic Oligonucleotide Synthesis (TiEOS): Its History, Prospects, and Challenges", Biochemistry, Mar. 13, 2018.
Lee, David F. et al., "Mapping DNA polymerase errors by single-molecule sequencing", Nucleic Acids Research, May 16, 2016.

* cited by examiner

*Primary Examiner* — David C Thomas
(74) *Attorney, Agent, or Firm* — Gerard M. Donovan; Reed Smith LLP

(57) ABSTRACT

Provided are methods and systems for encoding data into nucleic acid molecules. Methods and systems disclosed can include the use of promiscuous template nucleic acid molecules which enables data encoding using environmental modifications to yield encoded nucleic acid molecules.

20 Claims, 4 Drawing Sheets

SYSTEMS AND METHODS FOR DATA STORAGE IN NUCLEIC ACIDS

CROSS-REFERENCE TO RELATED APPLICATIONS

The present application claims priority to U.S. Provisional Application No. 62/644,533, filed Mar. 18, 2018, the entirety of which is incorporated herein by reference.

BACKGROUND

It is estimated that by 2040, the worldwide amount of stored data will be between $10^{24}$ bits and $10^{29}$ bits. Current electronic information storage technologies are based on physical chips that are made from silicon. However, silicon based technologies, such as flash memory, are estimated to have a scaling limit of 10 nm which equates to about 1 picogram per bit. Thus, in order to store all data by 2040 in such memory would require $10^{14}$ kilograms of wafer-grade silicon while projected supplies are orders of magnitude below this quantity. Even if wafer-grade silicon could be produced at higher rates, it is a non-renewable resource and will at some point be depleted.

Therefore, there is a need for data storage technologies that not only can store more information in a more compact form but which are also renewable and available in large quantities.

Nucleic acids are, in effect, the data storage system for biological organisms. By combining series of nucleotides in specific sequences, nucleic acids can encode proteins and provide a control system for protein synthesis in an organism. Nucleic acids, such as deoxyribonucleic acid (DNA), are also highly compact and can encode significant amounts of information in a small space. For example, DNA can encode 2 bits per 0.34 nm, more than 25-times the data storage density of flash memory. 1 kilogram of DNA can store $2 \times 10^{24}$ bits which would require more than $10^9$ kilograms of silicon flash memory to encode the same amount of information. In theory, a few kilograms of DNA could meet all of the world's data storage needs for centuries.

Nucleic acids are also a renewable resource. Because of the capacity for nucleic acids for encoding information in a small space and their renewability, they present an attractive option for data storage. However, there is a need for simple methods that can write data into a nucleic acid and that can be easily read.

DRAWINGS

For the purpose of illustrating the present disclosure, exemplary constructions of the disclosure are shown in the drawings. However, the disclosure is not limited to specific methods and instrumentalities disclosed herein.

DETAILED DESCRIPTION

Figure 1:
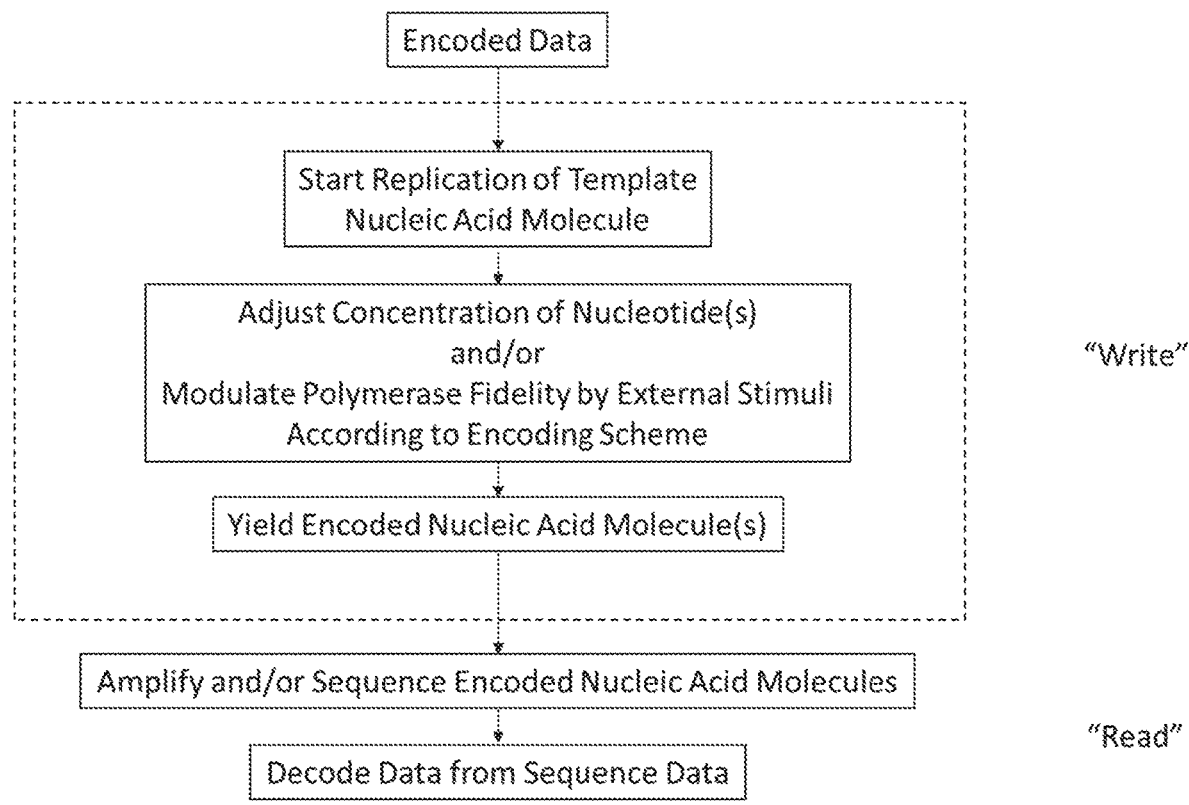
FIG. 1 depicts an exemplary workflow of a method of the present disclosure.

The present disclosure provides systems and methods for data storage and readout using nucleic acid molecules.

Definitions

Certain terminology is used in the following description for convenience only and is not limiting. Certain words used herein designate directions in the drawings to which reference is made. Unless specifically set forth herein, the terms "a," "an" and "the" are not limited to one element, but instead should be read consistent with the meaning of "one or more," "at least one," and "one or more than one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about," when used with a numerical value, is intended to include +/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

The term "promiscuous" as used herein to refer to a nucleotide or nucleic acid molecule means that the nucleotide or at least a portion of the nucleic acid molecule is capable of non-Watson-Crick base pairing. Non-promiscuous nucleotides, such as, by way of example but not limitation, adenine (A), guanine (G), cytosine (C) and thymidine (T) obey Watson-Crick base pairing—A pairs with T but not G or C and G base pairs with C but not A or T. By way of example but not limitation "promiscuous" nucleotides include 5-nitroindole, deoxyinosine triphosphate (dITP), and pyrimidine deoxynucleoside triphosphate (dYTP) which do not obey Watson-Crick base pairing rules. By way of further example, but not limitation, promiscuous bases are described in Loakes et al., *Survey and Summary: The Applications of Universal DNA Base Analogues*, Nucleic Acids Res. 29(12):2347-2447 (2001). As used herein to describe a polymerase, "promiscuous" describes a polymerase that can incorporate more than one nucleotide when replicating a template nucleic acid, in other words, the polymerase can add a nucleotide to the nascent strand that is not the canonical nucleotide according to Watson-Crick base pairing. For example, a promiscuous polymerase may incorporate different nucleotides into the nascent strand even when replicating the same nucleotide in a template molecule. The promiscuity of the polymerase may be a property of the polymerase or an inducible property under a given condition.

The term "nucleotide" as used herein refers to a molecule that contains a nitrogen-containing heterocyclic base, a sugar and one or more phosphate groups. For example, in some embodiments, a nucleotide can be a deoxynucleotide triphosphate (dNTP).

The term "non-natural nucleotide" as used herein refers to a nucleotide that obeys Watson-Crick base pairing but has a modification that can be detected. By way of example, but not limitation, such a modification can be a functional group attached to the nucleobase such as a methyl group on methylcytosine.

The present disclosure is directed to systems and methods for data storage in nucleic acid molecules and readout therefrom. Because of their compact size and high density storage capability, nucleic acid molecules represent an attractive data storage solution. The methods of the present disclosure rely on the presence or absence and/or degree of "incorporation" of nucleotides in a replicated strand to represent encoded data. The "incorporation" of different nucleotides can be affected by changes in the presence and/or concentration of a nucleotide in the reaction environment and/or "misincorporation" by the polymerase due to polymerase effectors that alter the properties of the polymerase such as the "error" rate. For example, by using a promiscuous template, different nucleotides can be incorporated into the nascent nucleic acid molecule during replication to encode bits of information. As another non-limiting example, promiscuous nucleotide(s) can be added to the reaction environment. As a further non-limiting example, a polymerase that can be modulated to increase its "error" rate can be induced to increase its "error" rate while in the presence of (or adding) a promiscuous nucleotide which can result in "misincorporation" of the promiscuous nucleotide when the canonical nucleotide is present. Such a method can be performed with a promiscuous template nucleic acid molecule or a non-promiscuous template nucleic acid molecule.

An exemplary workflow of a method of the present disclosure is shown in FIG. 1. Starting with encoded data, during the "write" portion of the method, replication of a template nucleic acid molecule is performed and the concentration of nucleotides and/or polymerase fidelity can be modulated. This results in encoded nucleic acid molecules which can include the coding nucleotides, thus storing the encoded data. If it is desired for the data stored in the encoded nucleic acid molecules to be retrieved ("read"), it can be obtained by sequencing or amplifying then sequencing the encoded nucleic acid molecules and decoded according the encoding schema.

In some embodiments, a method is provided for encoding data into a nucleic acid that includes providing encoded data, a template nucleic acid molecule, a primer, a polymerase, at least one non-coding nucleotide and a buffer. The template nucleic acid molecule can be a promiscuous nucleic acid molecule. The steps of the method may include combining the template nucleic acid molecule, primer, polymerase, at least one non-coding nucleotide and buffer to yield a reaction mixture. In some embodiments, a coding nucleotide is present in the reaction mixture. In other embodiments, a coding nucleotide is not present in the reaction mixture. Subsequently, the reaction mixture is incubated under conditions sufficient for the polymerase to extend the primer based on the template nucleic acid molecule. During the incubation, the concentration of a coding nucleotide in the reaction mixture may be adjusted in a time-dependent manner based on the encoded data according to an encoding scheme to yield an encoded nucleic acid molecule. Different coding nucleotides can be used and the adjustment of the concentration can include adding, removing or altering the concentration of the coding nucleotide in the reaction mixture.

In some embodiments, a method is provided for encoding data into a nucleic acid that includes providing encoded data, a template nucleic acid molecule, a primer, a polymerase, at least one non-coding nucleotide, a promiscuous nucleotide, and a buffer. The template nucleic acid molecule can be a promiscuous nucleic acid molecule. The steps of the method include combining the template nucleic acid molecule, primer, polymerase, at least one non-coding nucleotide, promiscuous nucleotide and buffer to yield a reaction mixture. Subsequently, the reaction mixture is incubated under conditions sufficient for the polymerase to extend the primer based on the template nucleic acid molecule. During the incubation, the fidelity of the polymerase is adjusted in a time-dependent manner based on the encoded data according to an encoding scheme to yield an encoded nucleic acid molecule. The adjustment in polymerase fidelity can be in response to stimulus that affects polymerase fidelity.

Encoded Data

Encoded data can refer to any form of stored data. By way of example, but not limitation, the data can be stored digitally, in electronic or biological format, and may contain additional information for decoding or reconstructing the data. For example, encoded data can be binary, however, any n-nary system of data encoding can be used. Because nucleic acids are not binary in nature—there are more than two types of nucleotides—information can be encoded by the use of different nucleotides and not solely a single coding nucleotide. For example, in methods of the present disclosure, different nucleotides can be added to a reaction mixture in a time-dependent manner to encode information according to a n-nary system, where n may be the number of different coding nucleotides. Additional information that may be included in the encoded data for decoding the data can include barcodes or other indicia for the location of the data in a larger data stream. By way of example, but not limitation, encoded data can include prefixes and suffixes that permit stitching of separate pieces of encoded data to generate a contiguous data stream.

In the context of data storage in a nucleic acid molecule, data can be encoded at the single nucleotide level or across a range of nucleotides. By way of example, but not limitation, a single bit of data such as a "0" or "1" can be encoded by the inclusion (or absence) of a particular nucleotide or by a rate of "incorporation" across a range of nucleotides. For example, in a 100-nucleotide long segment of the nucleic acid molecule, the presence of a particular nucleotide at a frequency above the standard incorporation or error rate of the polymerase can indicate a "0" or "1." Conversely, the presence (or absence) itself of a particular nucleotide at a probabilistic frequency in a given segment of the nucleic acid molecule can encode a "0" or "1." For example, if a completely promiscuous template nucleic acid molecule is used, the replicated strand can contain any nucleotides that are present in the reaction mixture. If a specific nucleotide is added, or "pulsed," into the reaction mixture, the frequency of incorporation of that specific nucleotide will be increased for a stretch of the replicated strand. The manner and amount in which the specific nucleotide is added and/or whether it is subsequently removed from the reaction mixture permits control of its incorporation into the nascent nucleic acid molecule. As such, at the time of decoding, along a stretch of the nucleic acid molecule, there will be an increase in the frequency of the nucleotide incorporation which can be analyzed via a probabilistic decoding scheme to determine whether the frequency of incorporation of the nucleotide indicates a "0" or "1" along that segment of the nucleic acid molecule. Such an exemplary embodiment is depicted in FIG. 1.

Figure 2:
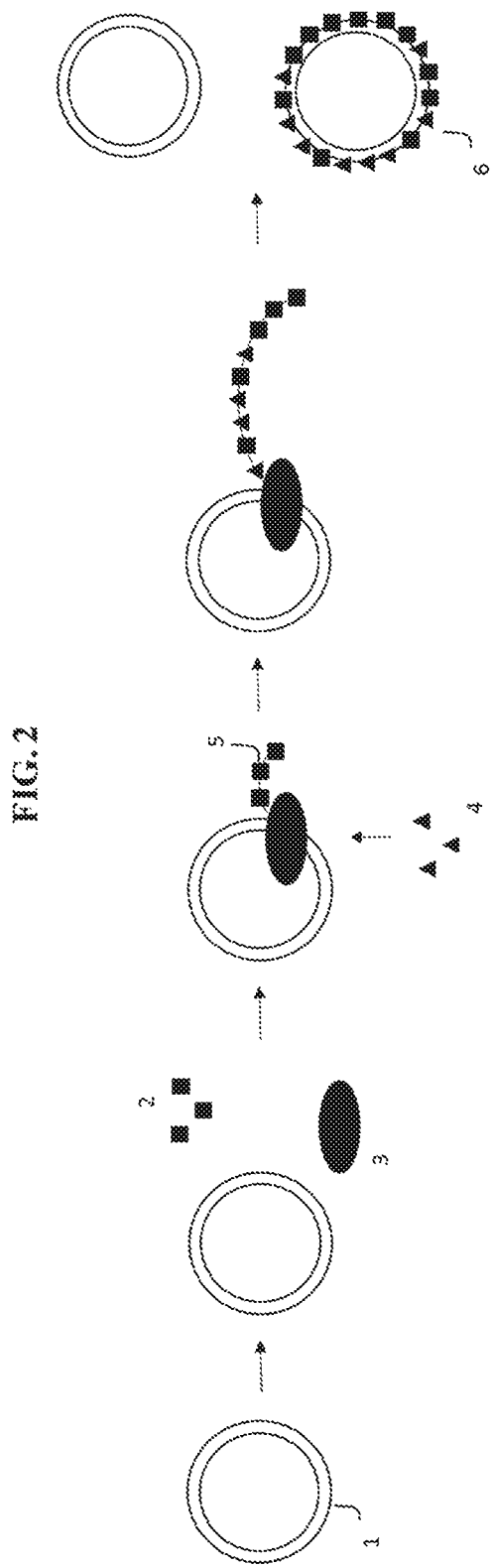
FIG. 2 depicts an exemplary embodiment of the present disclosure where a template nucleic acid molecule is replicated and coding nucleotides (triangles) are added to the reaction mixture to yield an encoded nucleic acid molecule.

As shown in FIG. 2, a fully promiscuous template nucleic acid molecule 1 is provided. Nucleotides 2, a polymerase 3 and a primer (not shown) are added and a replication reaction is performed. A coding nucleotide 4 is added to the reaction mixture at a time dependent upon the encoding scheme as the nascent strand 5 is being produced. By "pulsing" in the coding nucleotide 4, its presence in the nascent strand 5 is increased for a stretch of sequence. In FIG. 2 this is depicted by the incorporation of coding nucleotides 4 into the nascent strand 5 which decreases as the coding nucleotide is consumed, i.e. fewer coding nucleotides 4 are incorporated with increasing replication. The final product is an encoding nucleic acid molecule 6 which includes a sequence of nucleotides which exhibit an increased rate of incorporation of coding nucleotides 4 in a segment. When sequencing the encoded nucleic acid molecule, this increase in incorporation of coding nucleotides can be detected and interpreted according to the encoding scheme to obtain the encoded data.

Figure 3:
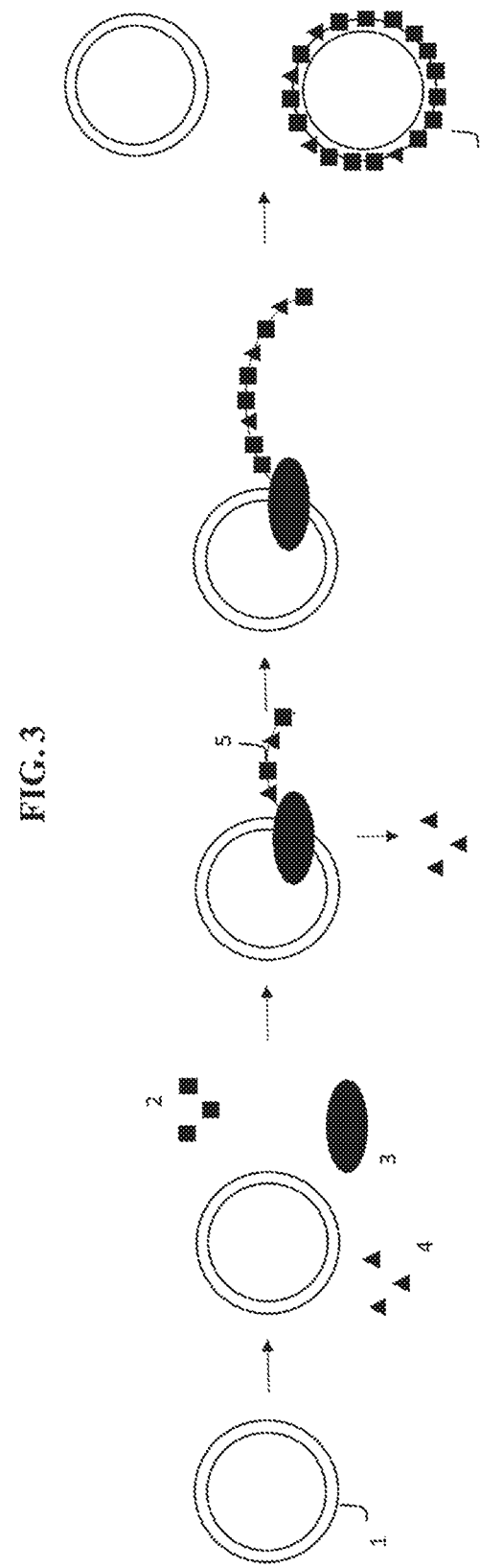
FIG. 3 depicts an exemplary embodiment of the present disclosure where a template nucleic acid molecule is replicated and coding nucleotides (triangles) are removed from the reaction mixture to yield an encoded nucleic acid molecule.

Similarly, in FIG. 3, an exemplary embodiment is depicted where, instead of adding a coding nucleotide 4, the coding nucleotides are present in the reaction mixture and are depleted, resulting in a decrease in the occurrence of the coding nucleotides 4 in the encoded nucleic acid molecule 6.

In some embodiments, a standard error rate or frequency of the occurrence or non-occurrence of a nucleotide that can indicate a bit of information and can be at least 1%, 2%, 3%, 4%, 5%, 6%, 7%, 8%, 9%, 10%, 15%, 20%, 30%, 40%, 50%, 60%, 70%, 80%, 90% or can be 100%.

Encoding and Decoding Schema

Any appropriate schema for encoding data can be used. The coding schema can depend on the rate of nucleotide incorporation for the polymerase because the amount of nucleotides added to a nascent strand per unit time in conjunction with adjustment of the reaction environment can determine the appropriate segment length for determining a bit of information. The encoding schema can also depend on the known error rate for the polymerase because the segment length can be adjusted based on known misincorporation rates. The encoding schema can also depend on the kinetics of the reaction and the rate at which coding nucleotides can be added, removed or be concentration adjusted. For example, an encoding scheme can be determined by the pre-defined rate of polymerase incorporation (or misincorporation) per unit time and the rate at which coding nucleotides can be added, removed or adjusted in the reaction mixture or by which the polymerase "error" rate can be modulated. In addition, the incorporation of non-promiscuous nucleotides in the template nucleic acid molecule in regular intervals can also be incorporated as a "clock" to separate arbitrary "sectors," with a certain number of "sectors" defining a bit of information. The number of "sectors" defining a bit of information can vary and can, by way of example, but not limitation, be 1, 2, 3, 4, 5, 6, 7, 8, 9, 10, 15, 20, 25, 30, 40, 50, 60, 70, 80, 90, 100, 200, 300, 400, 500, 600, 700, 800, 900, 1000 or more. In certain aspects, if the incorporation rate of the coding nucleotide is low, a longer sequence (for example, according to the Poisson distribution) can be required to encode a bit and an increased number of sectors can allow for greater reliability in decoding. In addition, by increasing the number of coding nucleotides present, e.g. non-natural nucleotides, more information can be encoded in the same number of base pairs. By way of example, but not limitation, with 4 nucleotides types in a reaction, there can be up to 2 bits of information encoded per base pair. Thus, increasing the number of coding nucleotides can increase informational density. In some embodiments, a first portion of the encoded nucleic acid molecule may not encode any useful information. By way of example, but not limitation, a first portion of the encoded nucleic acid molecule may not encode any of the data because of a "hot start" or limited polymerase fidelity during the early phase of DNA replication. In addition, some reading methods may not be effective for reading the first portion of the encoded nucleic acid molecule. By way of example but not limitation, in some instances Sanger sequencing may not accurately determine the first 50-100 nucleotides of a sequence. The first portion of the encoded nucleic acid molecule that is not used to encode the data can be of any appropriate length. In some embodiments, the first portion is 1 2, 3, 4, 5, 10, 15. 20, 25, 30, 40, 50, 60, 70, 80, 90, 100, 200, 300, 400, 500, 1000 nucleotides or more and any range therebetween.

By way of example, but not limitation, a template nucleic acid molecule could have the sequence:

PPPNNNPPPNNNPPPNNNPPPNNNPPPNNNPPPNNNPPPNNNPPPNNNPP PNNN, where P represents a promiscuous nucleotide while N represents a non-promiscuous nucleotide. As such, the template nucleic acid molecule is broken into sectors which are represented by each triplet of promiscuous nucleotides flanked by non-promiscuous nucleotides.

By way of example but not limitation, an encoding schema can be based on pulse density modulation.

By way of example, but not limitation, a signal processor can be used for information encoding and decoding. The signal processor can include a symbol processor, a frame processor and a high-level coding processor. The symbol processor uses components that include a rolling window, a histogram, an accumulator, a state machine, and threshold activation parameters. The frame processor composes multiple symbols for the symbol processor, and detects special sequences known as markers. The high-level processor can use concatenated codes, convolutional codes, and erasure codes such as Reed-Solomon. During encoding, the signal processor can use the high-level processor and then the frame processor to encode data. During decoding, the signal processor can use the symbol processor, then the frame processor and then the high-level processor. For example, during decoding the symbol processor can be given input of the raw sequence of nucleotides from an encoded nucleic acid molecule from a memory ticker tape object such as data from a long-read single-molecule nanopore DNA sequencer. The symbol processor can be designed using a state machine and an accumulator histogram using a rolling window. As the window rolls along the data, the histogram is updated based on the distribution of observed nucleotide types, which are each given a bucket in the histogram. Once one of the buckets in the histogram exceeds some parameterized threshold, the state machine emits an event proposing the possibility of detecting the start of the symbol. When the next "spike" of nucleotides are observed in the histogram, the conclusion of the current symbol will be detected and emitted by the symbol processor. The histogram window can be self-adjusting based on detecting whether the detected data is occurring slower or faster than some expected parameter which can be useful for timing recovery especially when one of the two bits (signal and no signal) can only be recovered by timing information and number of nucleotides processed. The symbol processor can emit symbols into the frame processor. During decoding, the frame processor can take each symbol and analyze sets of symbols for predetermined combinations known as markers, which can mark the beginning and end of frames of data. The frame processor can also choose to close a frame if a certain number of nucleotides have been passed, based on adjustable chosen parameters of the implementation. The frame processor can emit frames to the next layer. The next processor to receive data can be the high-level processor. The high-level processor can convert from frames of data to decoded data based on concatenated codes, convolutional codes, and erasure codes such as Reed-Solomon. The timing can be based on the number of observed nucleotides during processing. In some signal processing designs, the different processors can communicate with each other and report about timing problems and change parameters accordingly to "fix" the data stream.

Template Nucleic Acid Molecule

In the present disclosure, a template nucleic acid molecule can be provided which can be replicated by methods known in the art. By way of example, but not limitation, the template nucleic acid molecule can be replicated by polymerase chain reaction (PCR) or, where the template nucleic acid molecule is circular, by rolling circle amplification (RCA). In some embodiments, the template nucleic acid molecule is a promiscuous nucleic acid molecule. In some embodiments, the template nucleic acid molecule is completely promiscuous, i.e. it contains solely promiscuous nucleotides. In some embodiments, the template nucleic acid molecule is linear. In some embodiments, the template nucleic acid molecule is circular. In some embodiments, the template nucleic acid molecule comprises DNA. In some embodiments, the template nucleic acid molecule comprises RNA. Alternative nucleic acid molecules and nucleotides can be used in the template nucleic molecule and for incorporation by a polymerase and can include, by way of example, but not limitation, nucleic acids with alternative backbones such as XNA, PNA, TNA, and GNA. In some embodiments the template nucleic acid molecule is single-stranded. In some embodiments, the template nucleic acid molecule is double-stranded. In some embodiments, the resulting encoded nucleic acid molecule is single-stranded. In some embodiments, the resulting encoded nucleic acid molecule is double-stranded. In some embodiments the template nucleic acid molecule and/or the encoded nucleic acid molecule are partially double-stranded. By way of example but not limitation, the template nucleic acid molecule and/or encoded nucleic acid molecule can include portions that are double-stranded and portions that are single-stranded. In some embodiments, nucleic acid molecules can include more than one type of nucleic acid. By way of example, but not limitation, a nucleic acid molecule can include RNA for promiscuous nucleotides and DNA for non-promiscuous nucleotides.

Where a template nucleic acid molecule is promiscuous, it can act as a "blank tape." The promiscuous nucleotides in the template can act as "blanks" which allow for the incorporation of more than one different nucleotide. Thus, when replicating the template nucleic acid molecule, depending on the nucleotide content of the reaction environment, different nucleotides can be incorporated at promiscuous nucleotides in the template nucleic acid molecule. In some embodiments, the promiscuous template nucleic acid molecule can include a repeating sequence of alternating stretches of promiscuous and non-promiscuous nucleotides. By way of example but not limitation, the template nucleic acid molecule can include alternating repeats of promiscuous and non-promiscuous nucleotides such as repeats of 2, 3, 4, 5, 6, 7, 8, 9, 10, 15, 20, 25, 30, 40, 50, 60, 70, 80, 90, 100, 200, 300, 400, 500, 600, 700, 800, 900, 1000 or more nucleotides. In some embodiments, the alternating promiscuous and non-promiscuous repeats can be used to aid in encoding information by providing "breaks" between promiscuous and non-promiscuous regions. The non-promiscuous regions would generally include the "correct" nucleotides while the promiscuous regions would be subject to incorporation of the nucleotides present based on probability. Such probability may depend solely on the concentration of the nucleotides but may also depend on the polymerase used and the reaction conditions. By adjusting how and when the nucleotide(s) are incorporated, removed or adjusted in concentration, one can adjust the frequency of "misincorporation."

In the present disclosure, a template nucleic acid molecule can be of any size that can be replicated and/or sequenced. By way of example but not limitation, the template nucleic acid molecule (and resulting encoded nucleic acid molecule) can be 1, 10, 100, 500, 1,000, 5,000, 10,000, 25,000, 50,000, 100,000, 200,000, 300,000, 400,000, 500,000, 1,000,000, 1,500,000, 2,000,000 or more nucleotides long.

Coding Nucleotides

A coding nucleotide can be any nucleotide, the presence or absence of which (including the frequency of its occurrence) indicates encoded information. For example, the presence of a specific nucleotide or a frequency of the occurrence of the nucleotide within a stretch of a nucleic acid molecule can encode a bit of information. In some embodiments, the coding nucleotide is a non-promiscuous nucleotide. In some embodiments, the coding nucleotide is a promiscuous nucleotide. In some embodiments, the coding nucleotide is a modified nucleotide. Such modification to a nucleotide can be any suitable modification which makes the presence of the nucleotide detectable. By way of example, but not limitation, methylcytosine can be detected as different from cytosine when sequencing. Thus, the incorporation of methylcytosine as a coding nucleotide can be used to encode data by its incorporation into the encoded nucleic acid molecule. Non-limiting examples of modified nucleotides include 2-Amino-2'-deoxyadenosine-5'-Triphosphate, 5-Bromo-2'-deoxycytidine-5'-Triphosphate, 5-Bromo-2'-deoxyuridine-5'-Triphosphate, 7-Deaza-2'-deoxyadenosine-5'-Triphosphate, 7-Deaza-2'-deoxyguanosine-5'-Triphosphate, 2'-Deoxyinosine-5'-Triphosphate, 5-Propynyl-2'-deoxycytidine-5'-Triphosphate, 5-Propynyl-2'-deoxyuridine-5'-Triphosphate, 2'-Deoxyuridine-5'-Triphosphate, 5-Fluoro-2'-deoxyuridine-5'-Triphosphate, 5-Iodo-2'-deoxycytidine-5'-Triphosphate, 5-Iodo-2'-deoxyuridine-5'-Triphosphate, 5-Methyl-2'-deoxycytidine-5'-Triphosphate, 2-Thiothymidine-5'-Triphosphate, 2-Thio-2'-deoxycytidine-5'-Triphosphate, 5-Aminoallyl-2'-deoxycytidine-5'-Triphosphate, 5-Aminoallyl-2'-deoxyuridine-5'-Triphosphate, N4-Methyl-2'-deoxycytidine-5'-Triphosphate, 7-Deaza-7-Propargylamino-2'-deoxyadenosine-5'-Triphosphate, 7-Deaza-7-Propargylamino-2'-deoxyguanosine-5'-Triphosphate, 2'-Deoxyadenosine-5'-Triphosphate, 2'-Deoxycytidine-5'-Triphosphate, 2'-Deoxyguanosine-5'-Triphosphate, 2'-Deoxythymidine-5'-Triphosphate, Biotin-16-Aminoallyl-2'-dUTP, Biotin-16-Aminoallyl-2'-dCTP, Desthiobiotin-6-Aminoallyl-2'-deoxycytidine-5'-Triphosphate, 2'-Deoxyadenosine-5'-O-(1-Thiotriphosphate), 2'-Deoxycytidine-5'-O-(1-Thiotriphosphate), 2'-Deoxyguanosine-5'-O-(1-Thiotriphosphate), 2'-Deoxythymidine-5'-O-(1-Thiotriphosphate), 5-Aminoallylcytidine-5'-Triphosphate, 2-Aminoadenosine-5'-Triphosphate 5-Bromouridine-5'-Triphosphate, 5-Carboxycytidine-5'-Triphosphate, 5-Carboxymethylesteruridine-5'-Triphosphate, 7-Deazaadenosine-5'-Triphosphate, 5-Formylcytidine-5'-Triphosphate, 5-Formyluridine-5'-Triphosphate, 5-Hydroxycytidine-5'-Triphosphate, 5-Hydroxyuridine-5'-Triphosphate, 5-Hydroxymethylcytidine-5'-Triphosphate, 5-Hydroxymethyluridine-5'-Triphosphate, 5-Iodouridine-5'-Triphosphate, 5-Methoxycytidine-5'-Triphosphate, 5-Methoxyuridine-5'-Triphosphate, and $N^6$-Methyl-2-Aminoadenosine-5'-Triphosphate.

In some embodiments, a coding nucleotide can be capable of modification which can render the nucleotide detectable. Such modifications can include, by way of example but not limitation, osmylation or bisulfite treatment. By way of such modifications, the sequence of the encoded nucleic acid molecule can be read and the presence or frequency of the occurrence of the nucleotide determined. By way of example, but not limitation, nanopore sequencing can be used to determine the sequence of the encoded nucleic acid molecule for "reading" the encoded data. This information can then be decoded according to the encoding schema to determine the encoded data. In the case of bisulfite conversion, certain nucleotides can be converted such that they are detectable by sequencing. For example, in a nucleic acid molecule containing both cytosine and methylcytosine, treatment with bisulfite can convert the unmethylated cytosines to uracils which can be read as thymidines in Sanger sequencing, distinguishing between cytosine and methylcytosine. Non-limiting examples of modifiable nucleotides that can be modified after incorporation into a nucleic acid molecule include 5-Propynyl-2'-deoxycytidine-5'-Triphosphate, 5-Propynyl-2'-deoxyuridine-5'-Triphosphate, 5-Aminoallyl-2'-deoxycytidine-5'-Triphosphate, 5-Aminoallyl-2'-deoxyuridine-5'-Triphosphate, 7-Deaza-7-Propargylamino-2'-deoxyadenosine-5'-Triphosphate, 7-Deaza-7-Propargylamino-2'-deoxyguanosine-5'-Triphosphate, and 5-Aminoallylcytidine-5'-Triphosphate.

Polymerases

Polymerases useful in the methods and systems of the present disclosure can include polymerases that are capable of adding nucleotides to a nascent nucleic acid molecule from a template containing promiscuous nucleotides and/or those that are capable of adding promiscuous nucleotides to a nascent nucleic acid molecule and/or which are capable of having their fidelity affected by outside effectors.

Polymerases capable of adding nucleotides to a nascent nucleic acid molecule where the template nucleic acid molecule contains a promiscuous nucleotide are well known to those of skill in the art and can be identified by methods known in the art. For example, one of skill in the art can perform a replication method, such as PCR, using a promiscuous template nucleic acid molecule and determine whether the polymerase can add nucleotides to the nascent strand by known sequencing methods. Similarly, polymerases capable of adding promiscuous nucleotides to a nascent nucleic acid molecule are well known to those of skill in the art and can be identified by methods known in the art. For example, one of skill in the art can perform a replication method, such as PCR, using a template nucleic acid molecule and promiscuous nucleotides and determine whether amplification occurs by detecting the PCR products and/or known sequencing methods.

Depending on the type of nucleic acid molecule that the template nucleic acid molecule is, one of skill in the art can select the appropriate type of polymerase for replicating that type of nucleic acid.

By way of example, but not limitation, polymerases that can add nucleotides to a nascent nucleic acid molecule where the template includes a promiscuous nucleotide include phi29 polymerases. By way of example, but not limitation, other polymerases that can add nucleotides to a nascent nucleic acid molecule where the template includes a promiscuous nucleotide include Klenow fragment, Bst DNA polymerase, large fragment, Bsu DNA polymerase, large fragment, T5 DNA polymerase, and M-MULV reverse transcriptase.

By way of example, but not limitation, polymerases that can add promiscuous nucleotides to a nascent nucleic acid molecule include phi29, Klenow fragment, Bst DNA polymerase, large fragment, Bsu DNA polymerase, large fragment, T5 DNA polymerase, and M-MULV reverse transcriptase. In some embodiments, the polymerase is capable of adding a non-natural nucleotide—one that obeys Watson-Crick base pairing—but has a different chemical makeup that can be distinguished, for example functional groups—to the nascent nucleic acid molecule.

In some embodiments, a polymerase can be responsive to environmental effectors. Such responsiveness can be a native property of the polymerase or the polymerase can be engineered to have such a response. By way of example, but not limitation, the "error" rate of certain polymerases can be modified by environmental effectors such as ionic concentration, electrical stimuli, chemical stimuli, optical stimuli, non-optical radiation, temperature modulation and pH modulation. The speed or nucleotide preference of such polymerase can also, in certain aspects, be affected by the same environmental effectors. In some embodiments, where the "error" rate of a polymerase is increased by an environmental effector, a promiscuous nucleotide(s) can be added to a reaction mixture such that the polymerase has an increased probability of incorporating the promiscuous nucleotide as opposed to the canonical nucleotide when replicating a template nucleic acid molecule. This increase can, as defined herein, be used to encode information in the encoded nucleic acid molecule. Polymerases that are responsive to environmental effectors and methods for developing such polymerases are known in the art. By way of example, but not limitation, polymerases that are responsive to environmental effects can include Dpo4 and Klenow exo⁻ (D355A, E357A mutant of Klenow fragment, *E. coli* DNA polymerase I) which are both responsive to at least ion concentration. Changes in ion concentration can affect the polymerase fidelity of Dpo4 and Klenow exo⁻. In some embodiments, the polymerase responsive to environmental effectors is Dpo4 or Klenow exo⁻. In such embodiments, the environmental effector can be a change in ion concentration in the reaction mixture.

In some embodiments, the fidelity and other properties, by way of example but not limitation rate of replication, of polymerases can be modified by engineering methods known in the art. In some embodiments, the polymerase is an engineered polymerase. In some embodiments, the polymerase is modified to incorporate non-natural nucleotides and/or nucleotides containing universal bases. Examples of such polymerases and methods for generating them are presented in Laos, et al., *Frontiers in Microbiology*, 5:1-14 (2014) and in Loakes and Holliger, ChemComm 4619-4631 (2009). By way of example but not limitation, the polymerase can be engineered to incorporate ribonucleotides instead of deoxyribonucleotides. In some embodiments, the polymerase can be engineered to incorporate an expanded genetic "alphabet." In some embodiments, the polymerase can be engineered to incorporate nucleotides containing universal bases into the nascent strand.

By way of example but not limitation, ion fluxing can be performed by controlling the presence, absence or concentration of an ion or using electrical fields which can be turned on or off and/or modulated between set voltages and currents.

By way of example but not limitation, pH adjustment can be performed by addition of a strong acid or base or weak acid or base.

By way of example but not limitation, chemical stimulation can be performed by addition or removal of a small-molecule chemical to modulate the activity of the polymerase (e.g. error rate, polymerization speed, or dNTP preference) or the structure of the DNA molecule (e.g. melting temperature, base-pairing preference, helicity).

By way of example but not limitation, optical stimulation can be performed by applying visible or near-visible wavelengths of light to the reaction to effect a change in the structure of a protein (e.g. azobenzene unnatural amino acid incorporation in to the polypeptide) or to effect photocleavage of a chemical bond in a non-natural nucleotide or nucleotide-containing molecule to, for example, activate a nucleotide for incorporation into a DNA strand by a polymerase or deactivate a terminator nucleotide.

By way of example but not limitation, temperature modulation can be performed by altering the temperature of the reaction to induce a change in activity or specificity (error rate) of a polymerase or a structure of the DNA molecule, by active heating combined with passive cooling, or active cooling combined with passive heating, or both active heating and cooling.

The foregoing methods for affecting polymerase performance can be combined in certain aspects. For example, temperature-based control of pH can be performed due to weakening of a buffering agent's binding to a proton at higher temperatures to cause a decrease in pH. pH changes can also cause an increase or decrease in the chelation of a metal ion by another molecule, thus changing the effective free concentration of the ion in solution.

Exemplary non-limiting modifications of the polymerase can include mutation to, for example, remove or reduce exonuclease "proofreading" activity, increase natural misincorporation rate, or add functionality (by mutation, fusion, or chemical modification) that interacts with other modulation methods to induce a higher misincorporation rate in the enzyme.

Primers

In methods and systems of the present disclosure, any suitable primer for replication can be used that is compatible with the template nucleic acid molecule and polymerase. For readout and decoding, any suitable primer for amplification of the encoded nucleic acid molecule can be used. In some embodiments, the primer corresponds to an index sequence (addressability sequence) in the encoded nucleic acid molecule. The index sequence can identify the encoded nucleic acid molecule so that amplification and/or readout can be performed on specific encoded nucleic acid molecules. By way of example but not limitation, where multiple encoded nucleic acid molecules are produced with different and/or overlapping data, an index sequence in the encoded nucleic acid molecule can be used to identify each separate nucleic acid molecule and/or its position in a stream of data that is encoded by the multiple encoded nucleic acid molecules. By having a unique index sequence, each encoded nucleic acid molecule can be specifically amplified and/or read to decode the data without having to sequence or read each and every encoded nucleic acid molecule.

Addressability

Encoded nucleic acid molecules of the present disclosure can be made addressable by known methods in the art. In some embodiments, a DNA barcode can incorporated into the encoded nucleic acid molecule. This sequence can define the position of the encoded data in a larger data stream or otherwise identify the encoded nucleic acid molecule. In certain aspects, the DNA barcode can hybridize with a specific sequencing primer.

Encoded nucleic acid molecules can also be designed, based on the encoded data, to include a prefix and/or suffix sequence which can be used to identify the location of the encoded data in a larger data stream. This information can then be used to "stitch" together encoded data from separate encoded nucleic acid molecules.

In some embodiments, an "infix" can be included in the template nucleic acid molecule which is a unique barcode sequence that is repeated at a fixed interval which can be used to provide a constant indicator of a barcode.

In some embodiments, the physical location of the encoded nucleic acid molecule can be used to provide addressability and aid in decoding. By way of example, but not limitation, where the encoded nucleic acid is synthesized in a fixed position on a medium, such as, by way of example but not limitation, a single well or a spot on a microarray, that has other, different encoded nucleic acid molecules at different positions, for example, in other wells or spots, the position of the encoded nucleic acid molecule can provide addressability information and/or denote where the encoded data can be reconstructed in a larger data stream.

Multiplex Encoding and Decoding

Because the amount of encoded data to be stored in nucleic acid molecules can often exceed the capacity of the individual encoded nucleic acid molecules, encoded data can be broken into different segments which include portions of the encoded data, sometimes referred to as a larger data stream herein. As disclosed, barcoding and other addressability methods can be used to indicate the location of the encoded data of an encoded nucleic acid molecule in the larger data stream.

In some embodiments, where sequencing of multiple encoded nucleic acid molecules is performed, algorithms can be used to re-assemble the larger data stream. Such algorithms can include, by way of example but not limitation, stitching algorithms to reconstruct the data based on the most probable sequence of the data. In such embodiments, the data in different encoded nucleic acid molecules can overlap.

Where multiple encoded nucleic acid molecules are used, a unique sequence can be incorporated into some or all of the encoded nucleic acid molecules to distinguish between different encoded nucleic acid molecules. For example, the unique sequence can be used to match with a primer that can be used for amplification for subsequent sequencing to read specific encoded nucleic acid molecules. Thus, if one were to know the unique identifier(s) for a portion(s) of data one could amplify those specific encoded nucleic acid molecules without the need for maintaining separation of the encoded nucleic acid molecules. Thus, the storage of data in encoded nucleic acid molecules, in certain aspects, can be in a single composition, for example, a single tube.

Alternatively, spatial control over the location of the encoded nucleic acid molecules can also be employed. Where the individual reactions to generate each of multiple, different encoded nucleic acid molecules are maintained under physical separation, the location of the encoded nucleic acid molecules can denote information about the encoded data and its location in a larger stream. Thus, one could, knowing the location for particular portions of the data, "read" those specific locations with the relevant data by the applicable sequencing methods.

Environmental Control of Reaction Mixtures

The addition, depletion or adjustment of nucleotide concentrations in the reaction mixtures can be performed by known methods. Addition of nucleotides can be performed by flowing the nucleotides into the reaction mixture, by way of example but not limitation, by microfluidic channels, gates, valves, or direct physical addition such as by spraying by inket, electrospray or acoustic droplet ejection. Depletion or removal of nucleotides from a reaction mixture can be performed, by way of example but not limitation, by the use of a semi-permeable dialysis membrane that allows the flow of small molecules such as nucleotides but not larger molecules such as DNA, by passive depletion through diffusion, by active depletion, by charge-based concentration adjustment. Other exemplary non-limiting methods include adjusting the osmolarity of a solution on the other side of a semi-permeable membrane or via the flow of solutions of differing osmolarity into the reaction mixture where a semi-permeable membrane is used, or the use of an electric field to move the nucleotides across a semi-permeable membrane. Additional exemplary non-limiting methods for depletion of nucleotides can be performed by active removal of at least a portion of the reaction mixture solution while retaining the nascent encoded nucleic acid molecule which can be performed by immobilizing the template nucleic acid molecule (and nascent encoded nucleic acid molecule) via chemical immobilization on the surface of a reaction chamber or onto magnetic beads which can allow for reversible retention of the template nucleic acid molecule (and nascent encoded nucleic acid molecule) by an induced magnetic field. In some embodiments, the removal of a nucleotide can be performed by deactivation of the nucleotide which can be performed, by way of example but not limitation, by light-based chemical cleavage.

Systems for Carrying Out Methods of the Present Disclosure

Systems for carrying out the methods of the present disclosure can vary according to design choices known to those of skill in the art.

In some embodiments, a system of the present disclosure comprises a reactor. The reactor can be a reaction vessel or a predetermined location within the system where a reaction of the present disclosure can be carried out, such as a spot on a microarray. In some embodiments, the system comprises a plurality of reactors. In some embodiments the system further comprises a device for adding a nucleotide to the reactor. By way of example but not limitation, a device for adding a nucleotide to the reactor can be an inkjet head. In some embodiments, the systems comprises multiple devices for adding nucleotides to the reactor. By way of example, but not limitation, two or more inkjet heads could be configured to deliver nucleotides to a reactor where each is capable of adding a different nucleotide. In some embodiments, the system further comprises a device for removing a reaction solution from the reactor. In some embodiments, the system further comprises a semi-permeable membrane separating the reactor from a reservoir. The reservoir can be used to circulate a buffer solution, nucleotides, polymerase, template nucleic acid molecules, primers and/or other components of the reaction. In some embodiments, the semi-permeable membrane is capable of allowing nucleotides to pass through the semi-permeable membrane but not larger nucleic acid molecules such as DNA. In some embodiments, the semi-permeable membrane is capable of separating high molecular weight nucleic acid molecules for subsequent sequencing. In some embodiments, the system further comprises devices for altering the environment within the reactor. Such devices can be used to alter pH, temperature, introduce optical stimuli or other radiation, introduce chemical stimuli and/or ions, and/or produce electrical gradients.

In some embodiments, a reactor vessel can be a well, tube or other vessel. In some embodiments, a template nucleic acid molecule is immobilized on a surface of the reactor. For example, a template nucleic acid molecule can be immobilized on the surface of a semi-permeable membrane or on the bottom of a well.

Figure 4:
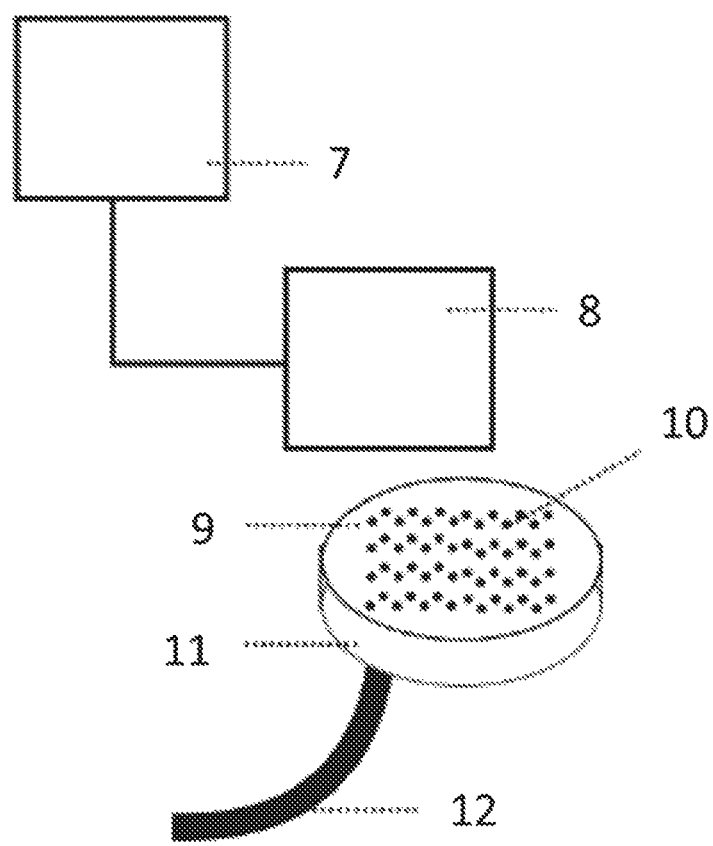
FIG. 4 depicts an exemplary system for carrying out the methods of the present disclosure.

An exemplary system of the present disclosure is show in FIG. 4 and includes 7 an input device for shuttling digital data to command modules 8 for inkjet printing to 9 template nucleic acid molecule page comprising a multitude of spots 10 onto which data is to be written. Each spot includes a template nucleic acid molecule immobilized on the page. A reservoir 11 under the template nucleic acid molecule page contains a nucleotide mixture, enzymes, templates, and buffering components, and has an attached drain 12; to avoid the need for pumps the reservoir may be set an angle or vertically in order to enhance diffusion using gravity in addition to or alternative to any established pressure differentials. The system further includes an inkjet nozzle corresponding to each spot of the array on the printing page (not shown) which can dispense a desired nucleotide onto the semi-permeable membrane. In operation, during "writing" of encoded data in each spot, the reservoir is able to circulate the nucleotide mixture, enzymes and buffering components while the inkjet heads are able to dispense coding nucleotides according to the encoding schema.

Sequencing Methods

Amplification and sequencing of encoded nucleic acid molecules can be performed by any suitable method. In some embodiments, a primer can be used in conjunction with a polymerase to amplify the encoded nucleic acid molecule. Sequencing can be performed by methods known in the art and can, by way of example, but not limitation include nanopore sequencing. By way of example, but not limitation, other methods for sequencing can include Sanger sequencing, sequencing by synthesis, single-molecule real-time sequencing, ion torrent sequencing, and pyrosequencing. By way of further example but not limitation, sequencing can include a step of protein-based modification of the encoded nucleic acid molecule such as using a poly-A binding protein that can attach or detach from the sequence based on the presence of certain nucleotides followed by modified nanopore sequencing. By way of further example, but not limitation, sequencing can be performed after treatment of the encoded nucleic acid molecules to modify the nucleotides such as by osmylation or bisulfate treatment.

In some embodiments, sequencing can involve measuring the frequency of occurrence of a nucleotide in a defined segment of an encoded nucleic acid molecule. Based on this measurement, the encoded data can be decoded according to the encoding scheme based on the frequency of occurrence of the nucleotide per a unit length of the nucleotide sequence of the encoded nucleic acid molecule. Thus, in certain aspects, the precise sequence of the encoded nucleic acid molecule need not be known with absolute certainty.

Kits

Kits containing the components to carry out the methods of the present disclosure are also contemplated. In some embodiments, such kits can include a template nucleic acid molecule, nucleotides, at least one coding nucleotide, a polymerase, and a primer. In some embodiments, a kit can further include a buffer. In some embodiments, a kit can further include a DNA binding protein.

The following examples are included to demonstrate preferred embodiments of the present disclosure. Those of skill in the art should, in light of the present disclosure, appreciate that many changes can be made in the specific embodiments which are disclosed and still obtain a like or similar result without departing from the concept, spirit and scope of the present disclosure.

EXAMPLES

Example 1: Encoding of Data Based on a Promiscuous Template

A promiscuous template nucleic acid molecule comprising a sequence of PPPNNNPPPNNNPPPNN NPPPNNNPPPNNNPPPNNNPPPNNNPPPNNNPPPNNN would be provided. Under this nomenclature, P represents a promiscuous nucleotide while N is a non-promiscuous nucleotide, M represents a base-pairing match for the non-promiscuous nucleotide while C represents a correctly incorporated nucleotide that matches the promiscuous nucleotide. In this example, P or M can be biased such that they are less likely to bind. For example, the P base can be biased toward triple hydrogen binding which would bias the encoded nucleic acid molecule away from having M where P is found in the template nucleic acid molecule.

When the promiscuous template nucleic acid molecule is replicated, it could yield a corresponding encoded nucleic acid with the sequence CCCMMMCCCMMMCCC MMMCQQMMMCQCMMMCCCMMMCCCMMM which would represent "misincorporation" (an increased frequency of incorporation) of Q. Upon decoding, or sequencing, of the encoded nucleic acid molecule, the increased frequency of incorporation of Q can be detected and, according the encoding schema, be determined to be a "1" or "0." This could be repeated for a longer template which would then encode more bits.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated. It is envisioned that various aspects described in the present disclosure can, within the scope of the present disclosure, be combined to the extent that they are not otherwise incompatible with one another without deviating from the spirit of the present disclosure.

What is claimed is:

1. A method for encoding data into a nucleic acid, comprising:
   providing:
   a) encoded data;
   b) a promiscuous template nucleic acid molecule, wherein at least a portion of said nucleic acid molecule comprises promiscuous bases;
   c) a primer, wherein at least a portion of said primer is complementary to a portion of said promiscuous template nucleic acid molecule;
   d) a polymerase;
   e) at least one non-coding nucleotide; and
   f) a buffer;
   combining said promiscuous template nucleic acid molecule, primer, polymerase, at least one dNTP, and buffer to yield a reaction mixture;
   incubating said reaction mixture under conditions sufficient for said polymerase to extend said primer based on said promiscuous template nucleic acid molecule; and
   adjusting a concentration of a coding nucleotide in said reaction mixture in a time-dependent manner, wherein adjusting the concentration of the coding nucleotide in said reaction mixture in a time-dependent manner comprises adding, removing, or altering the concentration of the coding nucleotide during the incubating step, based on said encoded data according to an encoding scheme to yield an encoded nucleic acid molecule.

2. The method of claim 1, wherein said encoded data is binary code.

3. The method of claim 1, wherein said promiscuous template nucleic acid molecule consists of promiscuous bases.

4. The method of claim 1, wherein said promiscuous template nucleic acid molecule comprises alternating repeats of promiscuous and non-promiscuous bases.

5. The method of claim 1, wherein said coding nucleotide is not present in said reaction mixture at the start of incubation, and wherein adjusting said concentration of said coding nucleotide is performed by adding said coding nucleotide to said reaction mixture.

6. The method of claim 5, further comprising removing at least a portion said coding nucleotide from said reaction mixture.

7. The method of claim 1, wherein said coding nucleotide is not present in said reaction mixture at the start of incubation, wherein said reaction mixture comprises at least two nucleotides at the start of incubation, and wherein adjusting said concentration of said coding nucleotide is performed by adding said coding nucleotide to said reaction mixture.

8. The method of claim 1, wherein said coding nucleotide is present in said reaction mixture at the start of incubation, wherein said reaction mixture comprises at least two nucleotides at the start of incubation, and wherein adjusting said concentration of said coding nucleotide is performed by removing said coding nucleotide to said reaction mixture.

9. The method of claim 1, wherein said template nucleic acid molecule is circular.

10. The method of claim 9, wherein said step of extension is rolling circle amplification.

11. The method of claim 1, wherein said encoded data contains an addressability sequence.

12. The method of claim 1, further comprising:
    sequencing said encoded nucleic acid molecule to obtain a nucleotide sequence of said encoded nucleic acid molecule; and
    decoding from said nucleotide sequence of said encoded nucleic acid the encoded data according to said encoding scheme based on the concentration of the coding nucleotide per a unit length of said nucleotide sequence of said encoded nucleic acid molecule.

13. The method of claim 1, further comprising:
    measuring the frequency of the occurrence of the coding nucleotide per each of a defined segment of the encoded nucleic acid molecule; and
    decoding from said measurement the encoded data according to said encoding scheme based on the frequency of the occurrence of the coding nucleotide per a unit length of said nucleotide sequence of said encoded nucleic acid molecule.

14. A method for encoding data into a nucleic acid, comprising:
  providing
    a) encoded data;
    b) a template nucleic acid molecule, wherein at least a portion of said nucleic acid molecule comprises promiscuous bases;
    c) a primer, wherein at least a portion of said primer is complementary to a portion of said promiscuous template nucleic acid molecule;
    d) a polymerase, wherein an error rate of said polymerase is increased in response to a stimulus;
    e) at least one non-coding nucleotide and a promiscuous nucleotide; and
    f) a buffer;
  combining said template nucleic acid molecule, primer, polymerase, at least one nucleotide non-coding nucleotide, promiscuous nucleotide, and buffer to yield a reaction mixture;
  incubating said reaction mixture under conditions sufficient for said polymerase to extend said primer based on said template nucleic acid molecule; and
  adjusting the fidelity of said polymerase in a time-dependent manner based on said encoded data according to an encoding scheme wherein adjusting the fidelity of said polymerase in a time-dependent manner comprises exposing said polymerase to said stimulus during the incubating step to yield an encoded nucleic acid molecule, wherein a frequency of incorporation of the promiscuous nucleotide into the encoded nucleic acid molecule is increased or decreased by the adjustment of the fidelity of the polymerase.

15. The method of claim 14, wherein said stimulus is ion fluxing.

16. The method of claim 14, wherein said template nucleic acid molecule is promiscuous.

17. The method of claim 14, further comprising
  sequencing said encoded nucleic acid molecule to obtain a nucleotide sequence of said encoded nucleic acid molecule; and
  decoding from said nucleotide sequence of said encoded nucleic acid the encoded data according to said encoding scheme based on the concentration of the coding nucleotide per a unit length of said nucleotide sequence of said encoded nucleic acid molecule.

18. The method of claim 14, further comprising:
  measuring the frequency of the occurrence of the promiscuous nucleotide per each of a defined segment of the encoded nucleic acid molecule; and
  decoding from said measurement the encoded data according to said encoding scheme based on the frequency of the occurrence of the promiscuous nucleotide per a unit length of said nucleotide sequence of said encoded nucleic acid molecule.

19. The method of claim 14, wherein said template nucleic acid molecule is circular.

20. The method of claim 19, wherein said step of extension is rolling circle amplification.

* * * * *